(12) United States Patent
Thom

(10) Patent No.: US 9,742,178 B2
(45) Date of Patent: Aug. 22, 2017

(54) MEDICAL DEVICE FEEDTHROUGH ASSEMBLIES WITH STRAIN RELIEF

(71) Applicant: Medtronic, Inc., Minneapolis, MN (US)

(72) Inventor: Andrew J. Thom, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 103 days.

(21) Appl. No.: 14/805,761

(22) Filed: Jul. 22, 2015

(65) Prior Publication Data

US 2016/0233656 A1    Aug. 11, 2016

Related U.S. Application Data

(60) Provisional application No. 62/028,988, filed on Jul. 25, 2014.

(51) Int. Cl.
*H02G 3/22* (2006.01)
*H01G 4/35* (2006.01)
*H02G 15/007* (2006.01)
*H01G 2/10* (2006.01)
*A61N 1/375* (2006.01)

(52) U.S. Cl.
CPC ............ *H02G 3/22* (2013.01); *A61N 1/3754* (2013.01); *H01G 2/103* (2013.01); *H01G 2/106* (2013.01); *H01G 4/35* (2013.01); *H02G 15/007* (2013.01)

(58) Field of Classification Search
CPC .. H02G 3/22; H02G 3/24; H02G 3/26; H02G 15/007; H02G 15/013; H02G 15/04; H01G 4/35; H01G 4/38; H01G 4/224; H01G 4/228; H01G 4/002; A61N 1/375; A61N 1/3754; A61N 1/3752
USPC ........ 174/50.5, 50.52, 50.53, 520, 650, 659; 439/909; 607/4, 5, 36, 37; 361/302, 307, 361/306.3, 298.4, 299.5, 306.1
See application file for complete search history.

(56) References Cited

U.S. PATENT DOCUMENTS

| | | | | |
|---|---|---|---|---|
| 5,531,003 | A * | 7/1996 | Seifried | H01B 17/28 361/302 |
| 5,817,984 | A * | 10/1998 | Taylor | A61N 1/3754 174/152 GM |
| 5,821,011 | A * | 10/1998 | Taylor | H01M 2/08 174/50 |
| 6,768,629 | B1 * | 7/2004 | Allen | A61N 1/3754 361/302 |
| 7,725,177 | B2 | 5/2010 | Iyer | |
| 7,839,620 | B2 | 11/2010 | Iyer et al. | |
| 8,927,862 | B2 * | 1/2015 | Barry | A61N 1/3754 174/50.56 |
| 8,982,532 | B2 * | 3/2015 | Iyer | A61N 1/3754 361/302 |
| 9,009,935 | B2 * | 4/2015 | Iyer | A61N 1/3754 361/302 |

FOREIGN PATENT DOCUMENTS

WO    2009/039006 A1    3/2009

* cited by examiner

*Primary Examiner* — Angel R Estrada

(57) ABSTRACT

Feedthrough assemblies for medical devices having various embodiments of strain relief members extending around portions of the feed through pin are described.

13 Claims, 5 Drawing Sheets

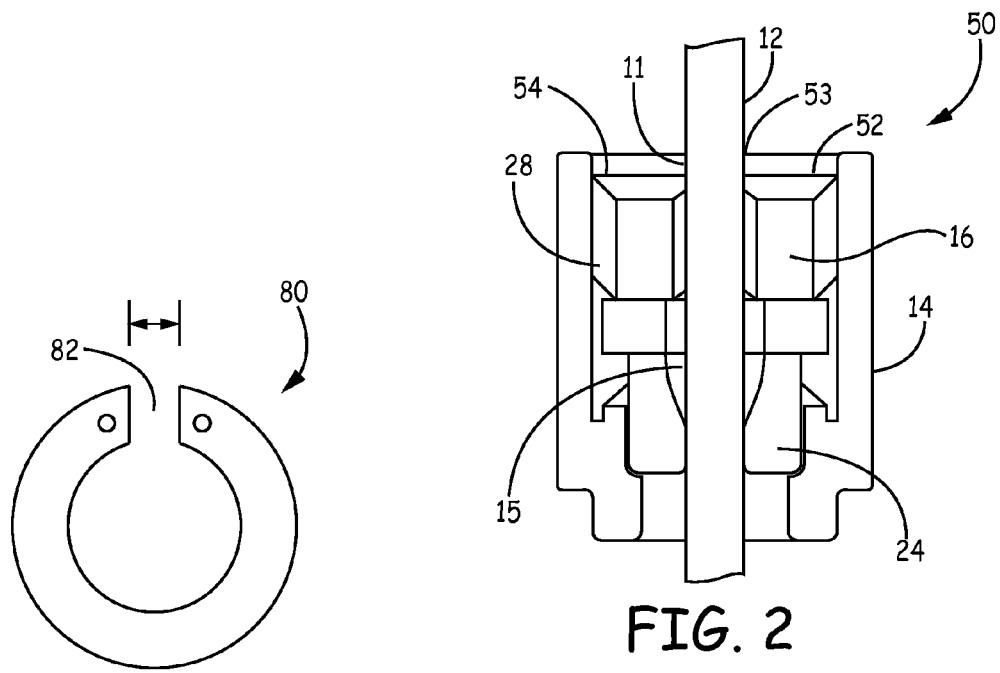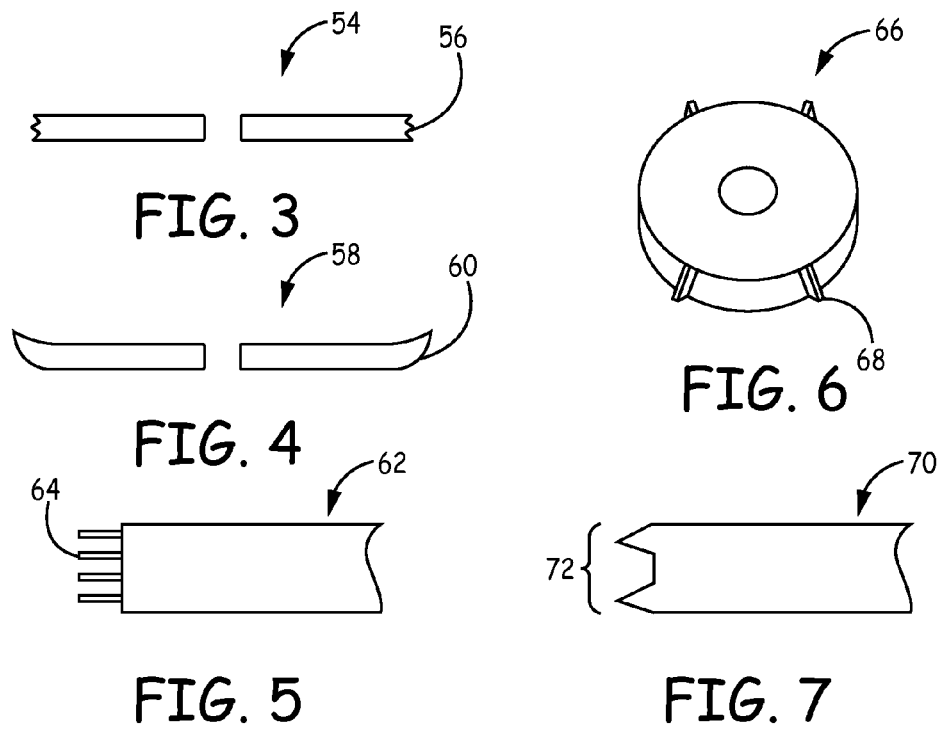

MEDICAL DEVICE FEEDTHROUGH ASSEMBLIES WITH STRAIN RELIEF

BACKGROUND

The present invention relates to feedthrough assemblies having means for proving strain relief, particularly strain relief members extending around feedthrough pins.

Feedthroughs are used to convey electrical or other signals from within a contained electrical device to the exterior of the electrical device. Hermetically sealed feedthroughs are used within medical devices such as implantable medical devices. It is desirable to provide feedthroughs having strain relief that is robust and easily attached to such feedthroughs.

SUMMARY

In one embodiment, a feedthrough assembly of this disclosure comprises a ferrule, a feedthrough pin extending through the ferrule, a filter capacitor extending around a first portion of the feedthrough pin within the ferrule, and a non-conductive strain relief member extending around a second portion of the feedthrough pin within the ferrule, the strain relief member frictionally fit within the ferrule.

In another embodiment, a feedthrough assembly of this disclosure consists essentially of a ferrule, a feedthrough pin extending through the ferrule, a filter capacitor extending around a first portion of the feedthrough pin within the ferrule, and a non-conductive strain relief member extending around a second portion of the feedthrough pin within the ferrule, the strain relief member frictionally fit within the ferrule. In this embodiment, "consisting essentially of" excludes for example the use of an adhesive in addition to a frictional fit, a strain relief member that has been heat or pressure deformed or both, and strain relief members made or formed from non-polymeric materials.

In another embodiment, a feedthrough assembly of this disclosure comprises a ferrule having a top edge and an outside surface, a feedthrough pin extending through the ferrule, a filter capacitor extending around a first portion of the feedthrough pin within the ferrule, and a non-conductive strain relief member extending around a second portion of the feedthrough pin and extending over the top edge and a portion of the outside surface of the ferrule, the strain relief member frictionally fit over the top edge of the ferrule.

In another embodiment, a feedthrough assembly of the disclosure consists essentially of a ferrule having a top edge and an outside surface, a feedthrough pin extending through the ferrule, a filter capacitor extending around a first portion of the feedthrough pin within the ferrule; and a non-conductive strain relief member extending around a second portion of the feedthrough pin and extending over the top edge and a portion of the outside surface of the ferrule, the strain relief member frictionally fit over the top edge of the ferrule. In this embodiment, "consisting essentially of" excludes for example the use of an adhesive in addition to a frictional fit, a strain relief member that has been heat or pressure deformed or both, and strain relief members made or formed from non-polymeric materials.

In another embodiment, an integral strain relief member of this disclosure comprises a non-conductive cup for use inside a device having an integral strain relief member, the integral strain relief member comprising a ferrule stabilization member, a feedthrough pin stabilization member defined by a channel, and a feedthrough pin placement cone, the channel being in-between and connecting the ferrule stabilization member and the feedthrough pin placement cone.

In another embodiment, a feedthrough assembly comprises a ferrule, a feedthrough pin extending through the ferrule, a filter capacitor extending around a first portion of the feedthrough pin within the ferrule, and an integral strain relief member, the integral strain relief member comprising a ferrule stabilization member, a feedthrough pin stabilization member defined by a channel, and a feedthrough pin placement cone, the channel being in-between and connecting the ferrule stabilization member and the feedthrough pin placement cone.

In another embodiment, a multipolar feedthrough assembly of this disclosure comprises a ferrule, multiple feedthrough pins extending through the ferrule, a filter capacitor extending around a first portion of each of the feedthrough pins within the ferrule, and a non-conductive strain relief member extending around a second portion of each of the feedthrough pins within the ferrule, the strain relief member frictionally fit within the ferrules.

In another embodiment, a multipolar feedthrough assembly of this disclosure comprises a ferrule, the ferrule having a top edge and an outside surface, multiple feedthrough pins extending through the ferrule, a filter capacitor extending around a first portion of each of the feedthrough pins within the ferrules and a non-conductive strain relief member extending around a second portion of the feedthrough pins and extending over the top edge and a portion of the outside surface of the ferrule, the strain relief members frictionally fit over the top edge of the ferrule.

In another embodiment, a multipolar feedthrough assembly comprises a ferrule, multiple feedthrough pins extending through the ferrule, a filter capacitor extending around a first portion of each of the feedthrough pins within the ferrule, and an integral strain relief member, the integral strain relief member comprising a ferrule stabilization member for the ferrule, a feedthrough pin stabilization member defined by a channel for each of feedthrough pins, and a feedthrough pin placement cone for each of the feedthrough pins, each of the channels being in-between and connecting the ferrule stabilization member and each feedthrough pin placement cone.

BRIEF DESCRIPTION OF THE DRAWINGS

FIG. 2 is a cross-sectional depiction of a feedthrough assembly for use in a medical device having a strain relieve member;

FIG. 3 shows another embodiment of a strain relief member;

FIG. 4 shows another embodiment of a strain relief member;

FIG. 5 shows another embodiment of a strain relief member;

FIG. 6 shows another embodiment of a strain relief member;

FIG. 7 shows another embodiment of a strain relief member;

FIG. 8 shows another embodiment of a strain relief member;

DETAILED DESCRIPTION

Feedthrough assemblies are used in medical devices, particularly implantable medical devices (IMDs) to provide an electrical connection between components within the shield or can of the device to components outside the shield of the device while also providing a hermetic seal from fluid ingress. Within such a feedthrough assembly, capacitors are frequently used as electromagnetic interference (EMI) filters to prevent undesirable signals from interfering with or damaging the IMD. In order to connect the capacitor to the rest of the feedthrough, a conductive material, such as solder, is used to provide an electrical joint and connection between a feedthrough pin and a filter capacitor. The electrical joint will be subject to device use conditions such as shock, vibration and deflection. Strain relief is used to mitigate the loss of the electrical connection due to electrical joint damage from such mechanical loading of the joint. The strain relief members described herein are positioned at or near the end of the ferrule that faces or extends within the shield of the device and distal from the filter capacitor. Various embodiments of feedthrough assemblies having strain relief members are disclosed in this application.

Figure 1:
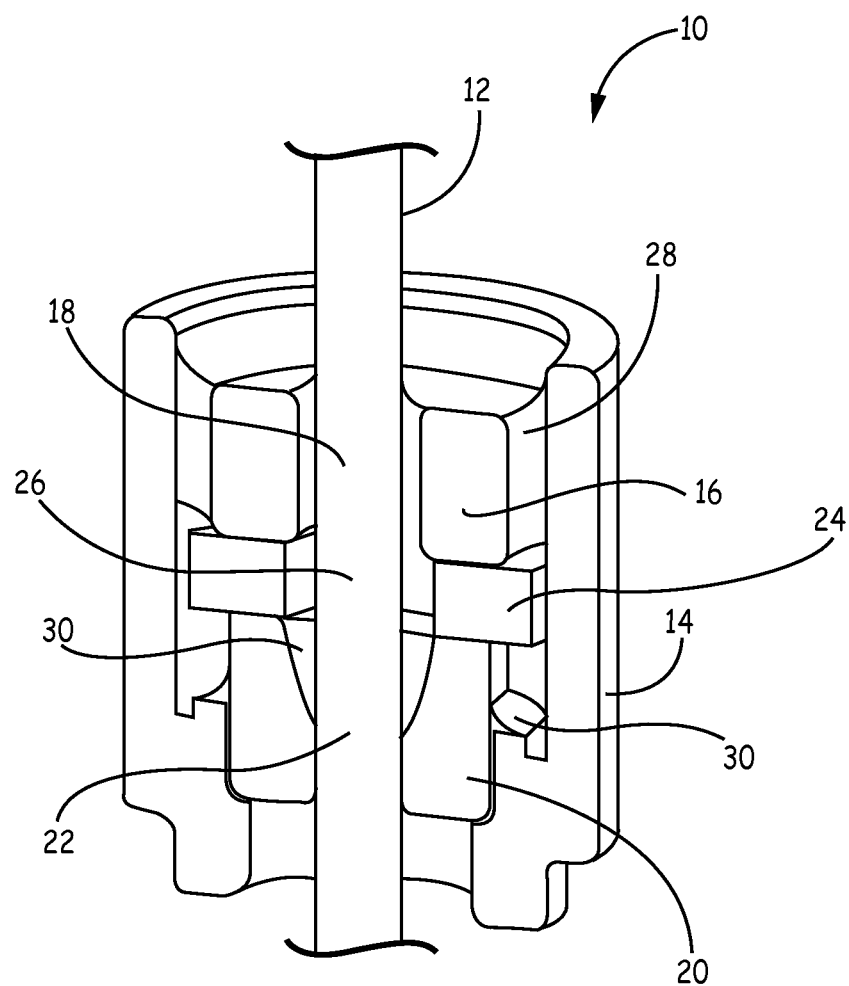
FIG. 1 is a cross-sectional depiction of a feedthrough assembly for use in a medical device.

FIG. 1 is a cross-sectional depiction of one example of a feedthrough assembly 10 for use in an implantable medical device. FIG. 1 is used to illustrate the various components of a typical feedthrough assembly for use in a medical device and such features are carried through the embodiments described below. Feedthrough assembly 10 includes a feedthrough pin 12 extending through a ferrule 14. Within ferrule 14 is a filter capacitor 16 extending around a first portion 18 of feedthrough pin, an insulator 20 extending around a third portion 22 of feedthrough pin and a non-conductive insulator 24 surrounding a fourth portion 26 of feedthrough pin.

Filter capacitor 16 is secured in place around the feedthrough pin 12 and within ferrule 14 by means of a conductive material joint 28, for example solder. Insulator 20 is secured in place around the feedthrough pin 12 and within ferrule 14 by braze material joint 30, for example gold braze. Non-conductive insulator 24 provides support within the ferrule for positioning the filter capacitor within the ferrule and is positioned in between insulator and filter capacitor. The non-conductive insulator 24 is designed to rest on insulator 20 and is not intentionally bonded to insulator 20 or filter capacitor 16 or feedthrough pin 12 or ferrule 14. This is done in part, along with not filling the space between the insulator 20 and ferrule 14, in order to maintain the ability to perform a helium leak check to ensure hermeticity of the braze material joint. In other embodiments, the non-conductive insulator can be omitted by including a ledge (not shown) within the ferrule on which the filter capacitor can directly rest.

Suitable materials for feedthrough pin 12 and ferrule 14 include titanium, niobium, platinum, platinum/iridium, molybdenum, zirconium, tantalum and alloys of these materials. Suitable materials for insulator include glass and ceramics, such as aluminum oxide. Suitable materials for non-conductive insulator include glass and ceramics such as aluminum oxide and non-conductive polymers. Typically, the filtering capacitor is a discoidal-type capacitor, for example containing barium titanate. The surface of a titanium ferrule to be soldered is coated or sputtered with titanium/nickel/gold layers and surfaces of the insulator to be brazed with gold are coated or sputtered with niobium.

FIG. 2 is a partial cross-sectional depiction of a feedthrough assembly 50 with an electrically insulating or non-conductive strain relief member 52. In this embodiment, strain relief member 52 extends around a first portion 11 of feedthrough pin 12 and strain relief member 52 is positioned within the ferrule 14. Strain relief member 52 is held in place by friction, that is, the strain relief member is frictionally fit or press-fit within the ferrule and against the inside surface 54 of ferrule. In this embodiment, strain relief member is generally planar and disk-shaped but could be molded or otherwise shaped to fit any unipolar or multipolar feedthrough assembly. In this embodiment, strain relief member is constructed or a molded or die cut non-conductive polymeric material such as polyether ether ketone (PEEK) or polytetrafluoroethylene (PTFE). The inner diameter of hole 53 of strain relief member 52 is designed to have minimum clearance to feedthrough pin 12 such that the lateral motion of feedthrough pin 12 in portion 18 of feedthrough pin is minimized during deflection of feedthrough pin 12. This in turn will minimize mechanical loading of solder material 54 at the inside diameter 15 of filter capacitor 16 and therefore minimize damage to the electrical interconnection of filter capacitor 16 to feedthrough pin 12. As an alternative to have minimum clearance between hole 53 of strain relief member 52 and feedthrough pin 12, the clearance could be larger and filled with an adhesive such as an epoxy-based adhesive.

FIGS. 3-7 are depictions of additional embodiments of non-conductive strain relief members 52 that can be frictionally fit or press fit into the ferrule 14. In the embodiment shown in FIG. 3, strain relief member 54 is generally planar and disk-shaped with ridges 56 on the edge of the strain relief member. The ridges 56 are integral with the strain relief member and are configured to flex and tightly contact the interior surface of ferrule 14 when the strain relief member 56 is pressed into ferrule. Ridges may be present on portions of or on the entire edge of the strain relief member.

In the embodiment shown in FIG. 4, strain relief member 58 is generally planar and disk-shaped with triangular-shaped members 60 on the edge of the strain relief member. The triangular-shaped members 60 are integral with the strain relief member and are configured to flex and tightly contact the interior surface of ferrule 14 when the strain relief member 58 is pressed into ferrule. Triangular-shaped members may be present on portions of or on the entire edge of the strain relief member.

In the embodiment shown in FIG. 5, strain relief member 58 is generally planar and disk-shaped with at least a plurality of finger-like projections 64 on the edge of the strain relief member 62. The finger-like projections 64 are integral with the strain relief member and are configured to flex and tightly contact the interior surface of ferrule 14 when the strain relief member 62 is pressed into ferrule. Finger-like projections may be present on portions of or on the entire edge of the strain relief member.

In the embodiment shown in FIG. 6, strain relief member 66 is generally planar and disk-shaped with a plurality of flap-like projections 68 on the edge of the strain relief member 66. The flap-like projections 68 are integral with the strain relief member and are configured to flex and tightly contact the interior surface of ferrule 14 when the strain relief member 66 is pressed into ferrule. The flap-like projections have major surfaces that are aligned substantially perpendicular to the major surfaces of the strain relief member 66. Flap-like projections may be present on portions of or on the entire edge of the strain relief member.

In the embodiment of FIG. 7, strain relief member 70 is generally planar and disk-shaped with two lines or rows of triangular-shaped members 72. The two rows of triangular-shaped members 72 are integral with the strain relief member and are configured to flex and tightly contact the interior surface of ferrule 14 when the strain relief member 70 is pressed into ferrule.

In the embodiment of FIG. 8, strain relief member 80 is generally planar and disk-shaped except having a gap 82 within the strain relief member 80. Strain relief member 80 is configured with a gap 82 that permits strain relief member to function as a spring. It is envisioned that strain relief member 80 is compressed such that gap 82 is closed, the strain relief member is placed into the ferrule and around feedthrough pin 12 and the tension in the strain relief member would be released, the gap 82 would open slightly, and strain relief member would be frictionally fit within the ferrule. In this embodiment, strain relief member would be typically made of a non-conductive polymeric material having sufficient rigidity and flexibility and spring-like characteristics to maintain the strain relief member in place after the strain relief member is placed into the ferrule.

Figure 9:
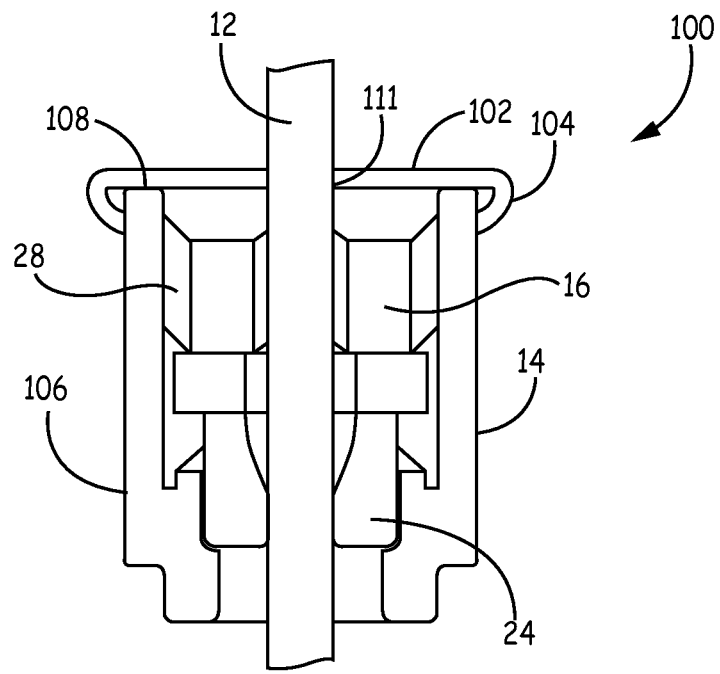
FIG. 9 is a cross-sectional depiction of a feedthrough assembly for use in a medical device having another embodiment of a strain relieve member.

FIG. 9 is a partial cross-sectional depiction of a feedthrough assembly 100 with a strain relief member 102. In this embodiment, strain relief member 102 extends around a fifth portion 111 of feedthrough pin 12 and curved ends 104 of strain relief member 102 contacts the outside surface 106 of ferrule. Curved ends 104 are configured to bend outwardly and exert a force against the outside surface of the ferrule sufficient to maintain the strain relief member in place. Strain relief member 102 is typically molded or is otherwise made from a non-conductive polymeric material having sufficient rigidity and flexibility to maintain the strain relief member in place after the strain relief member is placed onto the ferrule. It is envisioned that this embodiment of strain relief member would snap-fit or frictionally fit over the top edge 108 and a portion of the outside surface 106 of ferrule 14. The embodiment of strain relief member 102 shown in FIG. 9 can be formed or molded as a part or can be formed by overmolding strain relief member 102 over the feedthrough assembly by, for example, injection molding.

Figure 10:
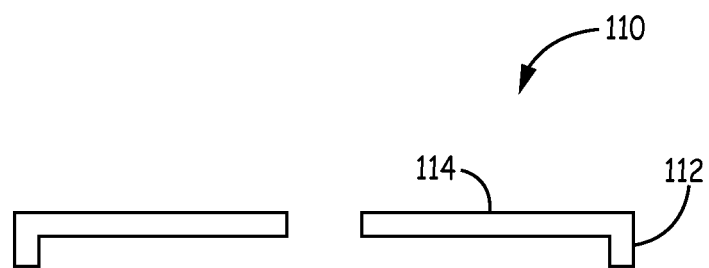
FIG. 10 shows another embodiment of a strain relief member

FIG. 10 shows another embodiment of strain relief member 110 that fits over the top edge and a portion of the outside surface of ferrule 14. In this embodiment, the ends 112 of strain relief member are substantially perpendicular to major surface 114 of strain relief member 110. Similar to the embodiment shown in FIG. 9, strain relief member 110 is configured to frictionally fit over the top edge 108 of ferrule and a portion of outside surface 106 of ferrule with enough friction and contact to maintain the position of the strain relief member. Strain relief member 110 is typically molded or is otherwise made from a non-conductive polymeric material having sufficient rigidity and flexibility to maintain the strain relief member in place after the strain relief member is placed onto the ferrule.

Figure 11:
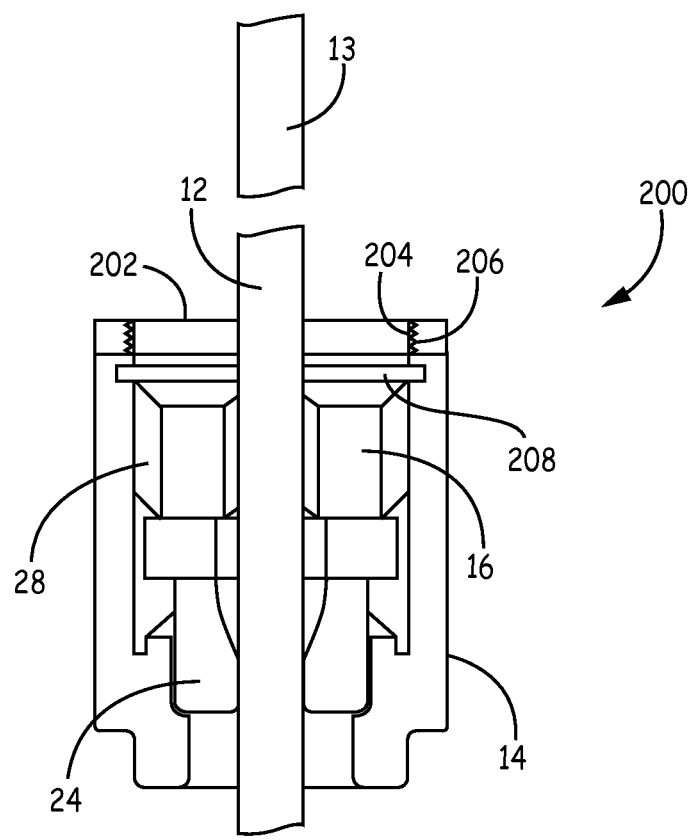
FIG. 11 is a cross-sectional depiction of a feedthrough assembly for use in a medical device having another embodiment of a strain relieve member.

FIG. 11 is a partial cross-sectional depiction of a feedthrough assembly 200 with a strain relief member 202. In this embodiment, strain relief member 202 extends around feedthrough pin 12 and has screw-like threads 204 which mate with corresponding ferrule threads 206. In this embodiment, strain relief member would be placed over the feedthrough pin and then rotated and screwed into the ferrule. Optionally, a retention member 208 can be placed around the feedthrough pin and within the ferrule, above the filter capacitor 16 and below the strain relief member 202. The retention member 208 can be similar in configuration to the strain relief member 80 shown in FIG. 8 to prevent over tightening of strain relief member 202 which could damage conductive material joint 28 if strain relief member was tightened such that it would contact conductive material joint. Retention member 208 is compressed and its edge is placed within groove in the inside surface of the ferrule. Similarly, such a groove could be used in the feedthrough assembly shown in FIG. 2 to maintain the placement of strain relief member 80 shown in FIG. 8 within the ferrule 14. Similarly, such a groove could be used on the outside surface of the ferrule shown in FIG. 9 to maintain the placement of strain relief member 102 on the ferrule 106 through fitment of curved ends 104 within such groove.

Figure 12:
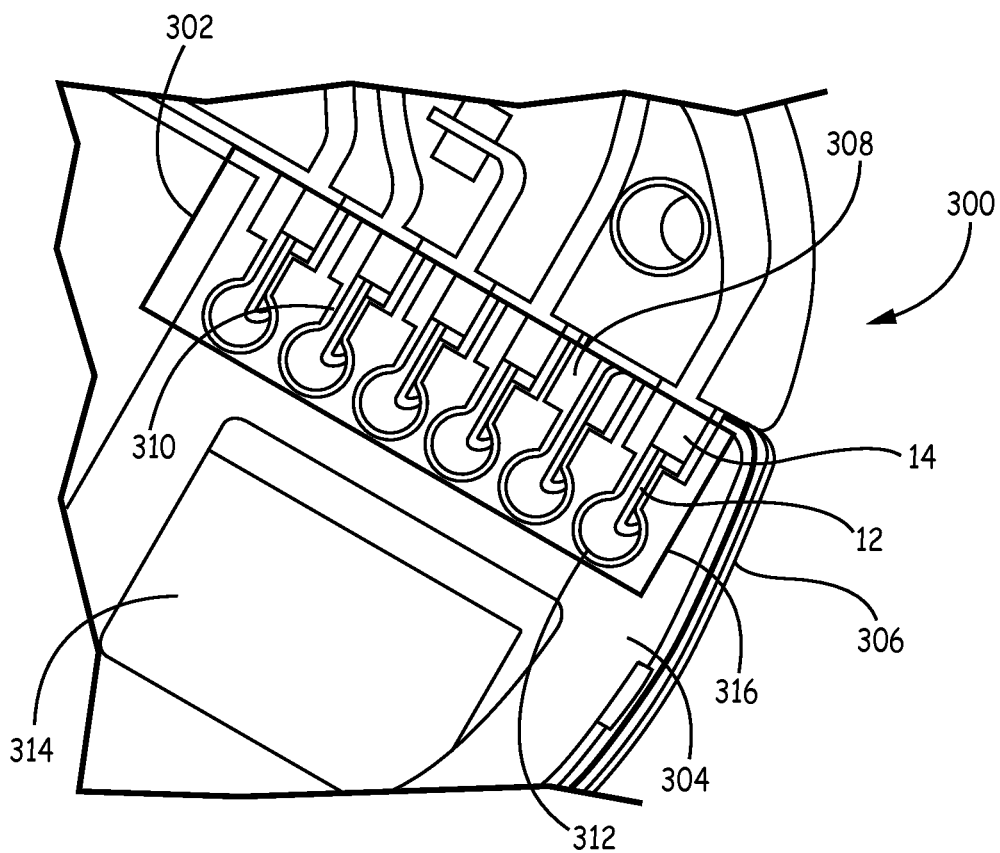
FIG. 12 is a partial perspective depiction of a partially assembled medical device showing an embodiment of an integral strain relief member.

FIG. 12 is a partial-perspective view of a depiction of a partially assembled medical device 300 showing a strain relief member 302 that is integral with an internal component stabilization member or cup 304. Cup 304 general is positioned and conforms to the interior contour of the device shield or can 306 to hold various components, for example, battery and circuit board in place to minimize movement of such internal components during use of the medical device. Integral strain relief member 302 includes ferrule stabilization member 308, feedthrough pin stabilization member 310 and feedthrough pin placement cone 312. Integral strain relief member 302 functions to rigidly hold the ferrule to cup 304, which in turn will minimize movement of circuit board 314. Minimizing the movement of circuit board 314 minimizes the movement of feedthrough pin 12 and therefore reduces strain imparted to conductive material joint 28.

Ferrule stabilization member 308 is shaped to accommodate the circumference of the ferrule so to provide a frictional fit or snap-fit to hold the ferrule in place. Feedthrough pin stabilization member 310 in this embodiment is defined by a groove or channel for a portion of the feedthrough pin to be held or stabilized within the channel and is located in between feedthrough pin stabilization member 310 and feedthrough pin placement cone. The width of the channel is configured to accommodate the diameter of the particular feedthrough pin used in the feedthrough assembly with a minimum clearance, without providing stress or force on the portion of the feedthrough pin contained within the channel. Feedthrough pin placement cone 312 is a cone-shaped guide cooperatively connected to the channel of the feedthrough pin stabilization member 310 and having a bore or hole at an end which approximately aligns with a connection hole in a circuit board 314 located (in this Figure) below the cup 304. Feedthrough placement cone 312 guides a pre-bent feedthrough pin to the connection hole in the circuit board below the feedthrough placement cone. After proper alignment and placement of the feedthrough pin into the circuit board, the feedthrough pin can be soldered or otherwise electrically connected to the circuit board.

Integral strain relief member 302 can be formed or molded into the cup 304 at the time the cup is formed or molded, generally of a non-conductive polymer such as PEEK. Optionally, the integral strain relief member may include a cover 316 (shown in dashed lines) to cover the exposed surface of feedthrough pin and ferrule.

Can 306 will have holes which will accept feedthrough 10 and feedthrough assembly 10 will then be hermetically joined to the hole in can 306 by for example, laser welding. Depending on the order and method of device assembly, sixth portion 13 of the feedthrough pin 12 (shown in FIG. 11) will be trimmed to a final length and then bent to an approximate 90 degree angle for providing first order strain relief to the conductive material joint 28. The position of the bend will be set so that sixth portion 13 of the feedthrough pin will fit into feedthrough pin placement cone 312 in cup 304 during assembly of the device. FIG. 12 shows a multipolar feedthrough assembly having multiple ferrules. Other multipolar feedthrough assemblies comprise multiple feedthrough pins within a single ferrule.

The invention claimed is:

1. A feedthrough assembly comprising:
a ferrule;
a feedthrough pin extending through the ferrule;
a filter capacitor extending around a first portion of the feedthrough pin within the ferrule; and
a non-conductive strain relief member extending around a second portion of the feedthrough pin within the ferrule, the strain relief member frictionally fit within the ferrule and wherein the non-conductive strain relief member has an edge and comprises ridges, triangular shaped members, finger-like projections, flap-like projections, or screw-like threads on the edge.

2. The feedthrough assembly of claim 1 wherein the non-conductive strain relief member comprises a polymeric material.

3. The feedthrough assembly of claim 1 further comprising a non-conductive adhesive on the strain relief member to hold the strain relief member in place in addition to the frictional fit.

4. The feedthrough assembly of claim 1 wherein the feed through assembly is a unipolar feedthrough assembly.

5. The feedthrough assembly of claim 1 wherein the feedthrough assembly is a multipolar feedthrough assembly.

6. A feedthrough assembly comprising:
a ferrule having a top edge and an outside surface;
a feedthrough pin extending through the ferrule;
a filter capacitor extending around a first portion of the feedthrough pin within the ferrule; and
a non-conductive strain relief member extending around a second portion of the feedthrough pin and extending over the top edge and a portion of the outside surface of the ferrule, the strain relief member frictionally fit and configured to snap fit over the top edge of the ferrule.

7. The feedthrough assembly of claim 6 wherein the non-conductive strain relief member has curved ends or substantially perpendicular ends.

8. The feedthrough assembly of claim 6 further comprising a non-conductive adhesive on the strain relief member to hold the strain relief member in place in addition to the frictional fit.

9. The feedthrough assembly of claim 6 wherein the strain relief member has ends or curved ends and further comprising a groove in an outside surface of the ferrule, the ends or the curved ends configured to snap-fit into the groove.

10. A feedthrough assembly comprising:
a ferrule;
a feedthrough pin extending through the ferrule;
a filter capacitor extending around a first portion of the feedthrough pin within the ferrule; and
an integral strain relief member comprising a non-conductive, polymeric cup for use inside a device having a polymeric integral strain relief member, the integral strain relief member comprising a ferrule stabilization member shaped to provide a snap-fit of the ferrule into the ferrule stabilization member, a feedthrough pin stabilization member defined by a channel, and a feedthrough pin placement cone, the channel being in-between and connecting the ferrule stabilization member and the feedthrough pin placement cone.

11. The feedthrough assembly of claim 10 wherein the feedthrough assembly is a multipolar feedthrough assembly having multiple ferrules.

12. A feedthrough assembly comprising: a ferrule; a feedthrough pin extending through the ferrule; a filter capacitor extending around a first portion of the feedthrough pin within the ferrule; and a non-conductive, polymeric strain relief member extending around a second portion of the feedthrough pin within the ferrule, the strain relief member frictionally fit within the ferrule; wherein the non-conductive strain relief member is planar and disc-like with a gap in the strain relief member wherein the gap permits the strain relief member to function as a spring.

13. The feedthrough assembly of claim 12 wherein the ferrule further includes a groove wherein an edge of the non-conductive strain relief member is fitted within the groove.

* * * * *